US011752351B2

(12) United States Patent
Stone et al.

(10) Patent No.: US 11,752,351 B2
(45) Date of Patent: Sep. 12, 2023

(54) SEALS FOR LEAD BORES OF IMPLANTABLE MEDICAL DEVICES

(71) Applicant: MEDTRONIC, INC., Minneapolis, MN (US)

(72) Inventors: Richard T. Stone, Minneapolis, MN (US); Michael T. Hegland, Mounds View, MN (US); Darren A. Janzig, Center City, MN (US); Dale F. Seeley, Spring Park, MN (US); Sean P. Skubitz, Forest Lake, MN (US); Ryan Davis, Plymouth, MN (US); Salil M. Vaidya, Maharashtra (IN)

(73) Assignee: MEDTRONIC, INC., Minneapolis, MN (US)

( * ) Notice: Subject to any disclaimer, the term of this patent is extended or adjusted under 35 U.S.C. 154(b) by 862 days.

(21) Appl. No.: 16/579,579

(22) Filed: Sep. 23, 2019

(65) Prior Publication Data
US 2021/0085983 A1 Mar. 25, 2021

(51) Int. Cl.
*A61N 1/37* (2006.01)
*A61N 1/375* (2006.01)
*A61M 39/00* (2006.01)
*A61F 2/30* (2006.01)

(52) U.S. Cl.
CPC ............ *A61N 1/3752* (2013.01); *A61M 39/00* (2013.01); *A61F 2002/3007* (2013.01); *A61M 2039/0054* (2013.01)

(58) Field of Classification Search
CPC .... A61M 39/00; A61N 1/3752; A61N 1/3754

USPC ............................................................. 607/2
See application file for complete search history.

(56) References Cited

U.S. PATENT DOCUMENTS

| | | | |
|---|---|---|---|
| 8,092,260 B2 * | 1/2012 | Sjostedt ............. | H01R 13/5224 439/669 |
| 8,140,163 B1 * | 3/2012 | Daglow ............... | H01R 13/193 607/36 |
| 8,215,013 B2 * | 7/2012 | Dilmaghanian ..... | H01R 13/521 29/877 |
| 9,682,242 B2 * | 6/2017 | Dilmaghanian ....... | F16J 15/025 |
| 2002/0107555 A1 * | 8/2002 | Rusin ................... | A61N 1/3752 607/37 |
| 2004/0078062 A1 * | 4/2004 | Spadgenske ......... | A61N 1/3752 607/37 |
| 2007/0100386 A1 | 5/2007 | Tronnes | |
| 2007/0225772 A1 | 9/2007 | Lahti et al. | |
| 2011/0059639 A1 | 3/2011 | Dilmaghanian | |

(Continued)

OTHER PUBLICATIONS

PCT/US2020/048071 International Search Report and Written Opinion, dated Nov. 13, 2020.

*Primary Examiner* — Eric D. Bertram
(74) *Attorney, Agent, or Firm* — WITHERS & KEYS, LLC

(57) ABSTRACT

Seals used within lead bores of implantable medical devices for creating a seal to implantable medical leads inserted into the lead bores include a cylinder that engages the lead body. The length of contact of the cylinder to the lead body is at least 0.010" long while average contact pressure is no greater than (10 pounds per inch)/(contact length). Adequate electrical isolation is achieved, even when a debris particle is present between the inner cylinder and the lead body while insertion force remains acceptable.

20 Claims, 4 Drawing Sheets

(56) References Cited

U.S. PATENT DOCUMENTS

| | | | | |
|---|---|---|---|---|
| 2012/0185019 A1* | 7/2012 | Schramm | ............. | A61N 1/3752 |
| | | | | 607/72 |
| 2012/0315798 A1* | 12/2012 | Poon | ...................... | H01R 24/58 |
| | | | | 439/668 |
| 2013/0150915 A1* | 6/2013 | Kane | .................. | A61N 1/37512 |
| | | | | 607/36 |
| 2014/0094048 A1* | 4/2014 | Dilmaghanian | ... | H01R 13/2421 |
| | | | | 29/874 |
| 2019/0192861 A1* | 6/2019 | Lopez | ................ | A61N 1/36128 |

\* cited by examiner

SEALS FOR LEAD BORES OF IMPLANTABLE MEDICAL DEVICES

TECHNICAL FIELD

Embodiments relate to seals that are placed in lead bores of implantable medical devices.

BACKGROUND

A lead bore of implantable medical device includes one or more electrical connectors that make an electrical connection to corresponding electrical contacts on a proximal end of an implantable medical lead that is inserted into the lead bore. Conductors within the implantable medical lead carry electrical signals between the electrical contacts and electrodes located near a distal end of the lead. These electrical signals may be stimulation signals being delivered to tissue at the distal electrodes. These signals may additionally or alternatively be sensed physiological signals occurring at distal electrodes that are delivered to the sensing circuitry of the implantable medical device.

When carrying stimulation signals or sensed signals on the implantable medical lead, it is useful to electrically isolate the electrical contacts on the proximal end from each other as well as from the body tissue surrounding the implantable medical device. For instance, such isolation helps a signal intended for a given proximal contact and corresponding distal electrode to be delivered to that proximal contact and distal electrode while largely preventing any amount of the signal from leaking to the body or other proximal contact at the proximal end of the lead. Likewise, such isolation helps a sensed signal obtained at a given distal electrode to be delivered to the circuit path of the implantable device corresponding to the proximal contact paired to that distal electrode while largely preventing any amount of the signal from leaking to the body or other proximal contact at the proximal end of the lead. Likewise, other electrical signals present nearby the implantable medical device may be largely blocked from leaking into the lead bore.

Electrical isolation is provided by the presence of seals within the lead bore of the implantable medical device. These seals typically are present between adjacent electrical connectors within the lead bore and also at the lead bore entrance at the surface of the implantable medical device. These seals may generally provide circumferential protrusions with an open center that has a smaller diameter than the lead diameter so that contact is made at the open center with the lead body to provide a seal about the lead body.

While a seal is formed, movement of the lead body in radial directions may stretch the opening of the protrusions which may form a small gap that allows small amounts of body fluid to pass by the seal. This lead body movement may occur during implantation or during normal body movement by the patient. Furthermore, debris may also become lodged between the seal and the lead body and create such a gap. While the small amount of fluid may not always be a concern, for situations where the electrical signals of interest are already very small yet other nearby signals are large, such as when a relatively small neurological signal of the brain is being sensed while relatively large cardiac signals are present near the implantable medical device, a small amount of fluid ingress to the lead bore may cause enough signal leakage to be problematic.

SUMMARY

Embodiments address issues such as these and others by providing a seal for an implantable medical device that includes a cylindrical portion that engages the lead body. Rather than a point of contact to the lead body created by a radially inward protrusion that has a fixed position, the cylindrical portion makes contact along a relatively long length of the lead body to establish adequate electrical isolation but with a relatively low average contact pressure to avoid high insertion force requirements.

Embodiments provide an implantable medical system that includes a lead and a housing defining a lead bore having a lead bore diameter where the lead is present within the lead bore. Circuitry is present within the housing and an electrical connector is positioned within the lead bore and electrically coupled to the circuitry. An elastic seal body is coupled to the housing, and the elastic seal body includes a first cylinder defining a seal bore having a centerline. The first cylinder is positioned within the lead bore and contacts the lead body over more than 0.010 inch of length of the lead body and with an average contact pressure of no greater than (10 pounds per inch)/(contact length). A wall portion of the elastic seal body is coupled to the housing, and the wall portion is coupled to the first cylinder with the first cylinder having a resting position where the centerline forms a first angle with respect to a first plane. The first cylindrical portion is movable relative to the wall portion to allow the first angle of the centerline with respect to the first plane to change.

Embodiments provide a method of providing electrical isolation of an electrical contact of a therapy delivery element within a surrounding structure having a first bore containing an electrical connector. The method involves providing an elastic seal body within the first bore and coupled to the surrounding structure, the elastic seal body comprising a first cylinder defining a seal bore configured to receive a portion of the therapy delivery element and to establish electrical contact between the therapy delivery element and the electrical connector of the first bore. The method further involves creating contact of the first cylinder with the portion of the therapy delivery element over a contact length of at least 0.010 inches with an average contact pressure of no greater than (10 pounds per inch)/(contact length) when the portion of the therapy delivery element is received by the first cylinder.

Embodiments provide an implantable medical system that includes a lead having a proximal contact and a lead body. The implantable medical system also includes a lead extension comprising a distal end structure defining a lead bore containing an electrical connector and at least one elastic seal body, the elastic seal body comprising a first cylinder. The lead is present within the lead bore such that the proximal contact makes contact with the electrical connector and wherein the first cylinder contacts the lead body over a contact length of at least 0.010 inches and with an average contact pressure of no greater than (10 pounds per inch)/(contact length).

The embodiments described herein are discussed primarily in regard to a header mounted to a housing of an implantable medical device for accepting a proximal end of a lead. However, this should not be considered a limitation. The described seal elements may be incorporated into any aspect of an implantable system that requires a seal element that couples to a movable member that may move relative to a wall portion of the seal element. For example, this type of seal element may likewise be employed at a distal end of a lead extension that is to receive a proximal end of a lead.

DETAILED DESCRIPTION

Embodiments provide seals for lead bores of implantable medical devices. Embodiments provide for a seal contact length of more than 0.010" to the lead body while maintaining an average contact pressure of no greater than (10 pounds per inch)/(contact length). Some embodiments may further allow the lead to move radially out of center-alignment relative to the lead bore while maintaining a sealing engagement to a lead body of the lead.

Figure 1:
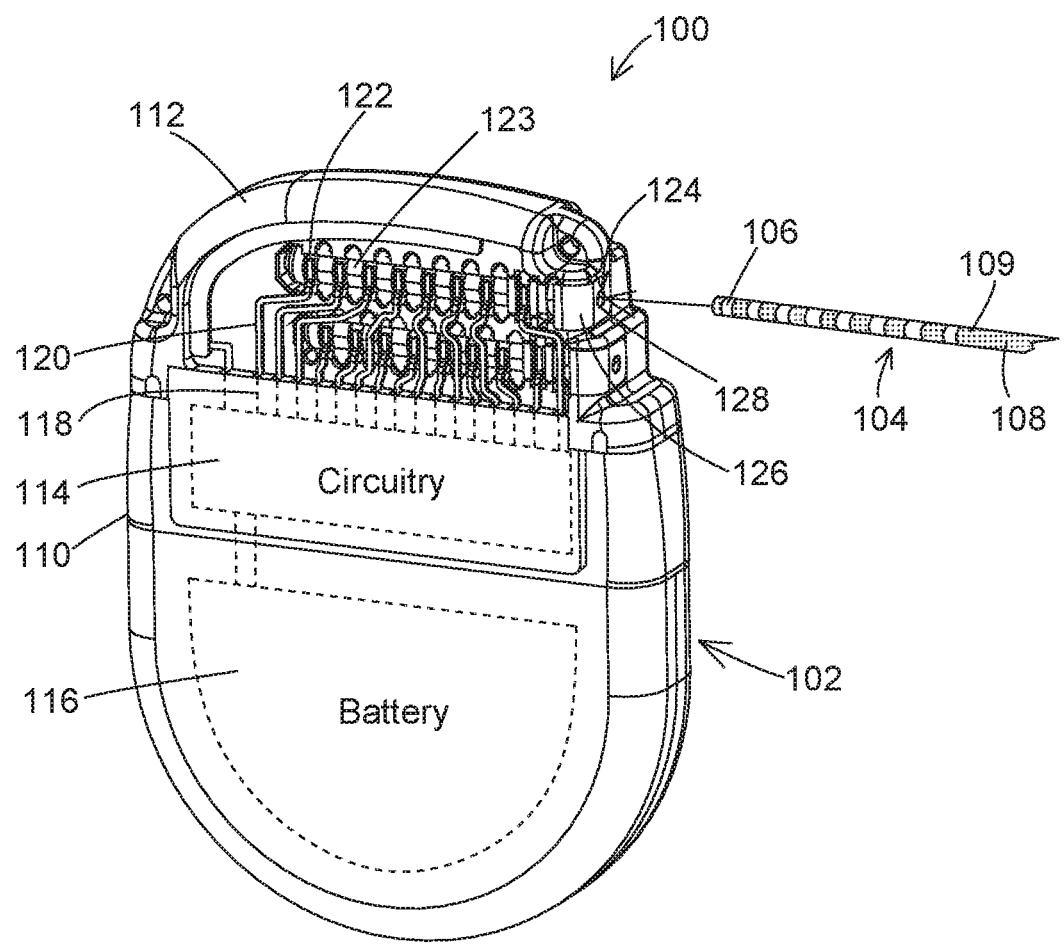
FIG. 1 shows an example of an implantable medical system including an implantable medical lead and an implantable medical device that may include seals according to the various embodiments.

FIG. 1 shows an implantable medical system 100 that includes an implantable medical device 102 and an implantable medical lead 104. The implantable medical device 102 includes a circuitry housing 110 and a header 112 mounted to the circuitry housing 110 that together form a complete device housing. The circuitry housing 110 provides a sealed enclosure for circuitry 114 and an associated battery 116 that powers the circuitry. The circuitry 114 may include a stimulation engine capable of producing stimulation pulses. The circuitry 114 may also or alternatively include a sensing circuit capable of receiving physiological signals. Examples of the implantable medical device 102 include but are not limited to neurostimulators such as those for deep brain, spinal cord, pelvic, or peripheral nerve sensing and/or stimulation. Such a device may be used to deliver electrical stimulation therapy and, in some case, also deliver a therapeutic agent, to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. In other examples, such a device may be a cardiac device used to deliver electrical stimulation to the heart.

In order to deliver the electrical signals, the circuitry 114 has electrical connections 118 that establish electrical pathways to conductors 120 present within the header 112. The electrical connections 118 may include feedthroughs that allow the electrical pathways to transition between the interior of the circuitry housing 110 and the interior of the header 112 while maintaining a sealed relationship between the circuitry housing 110 and the header 112.

The header 112 provides a lead bore 124 that includes a set of electrical connectors 122. The conductors 120 are electrically coupled to the corresponding electrical connectors 122 to deliver the electrical signals. The lead bore 124 also includes a set of seals 123 that are interleaved with the electrical connectors 122. A front seal 126 also provides an exterior surface for the header 112 in the area at the opening of the lead bore 124. In this particular example, there is a second lead bore also containing electrical connectors with interleaved seals. While the conductors 120, electrical connectors 122, and seals 123 are visible in FIG. 1, they are enclosed in a sealed arrangement with the header 112 by a layer of liquid silicone rubber or other similar material.

A proximal end of the implantable medical lead 104 is shown. On this proximal end, the lead includes proximal contacts 106 mounted to a lead body 108. These proximal contacts are conductors such as metal rings. Conductors inside the lead body 108 electrically couple the proximal contacts 106 to distal electrodes located on the distal end of the lead 104.

The proximal end of the lead 104 is inserted into the lead bore 124 of the implantable medical device 102. Each proximal contact 106 electrically couples to a corresponding electrical connector 122. Each seal 123 engages the lead body 108 between adjacent proximal contacts 106. The front seal 126 engages the lead body 108 distally of the most-distal proximal contact 106. In this example, because the front seal 126 provides an outer surface of the header 112 at the lead bore 124, the front seal 126 includes an opening 128. This example of the lead 104 also includes a surface coating 109, such as a siloxane or parylene coating, that reduces friction as the lead body 108 passes through the front seal 126. This surface coating 109 may be effective for certain configurations of the front seal 126 that might otherwise creation an undesirable amount of insertion friction.

While this discussion of FIG. 1 has been in relation to the front seal 126, it will be appreciated that a similar structure as discussed below in relation to FIGS. 2-6 may be used at other seal locations within the header 112. Furthermore, it will be appreciated that while FIGS. 2-6 show one seal orientation, the seal orientation could be reversed where the front side becomes the rear side and vice versa. It will additionally be appreciated that while the examples show a single inner cylinder, multiple inner cylinders could be used, such as an inner cylinder at the front of the front seal 126 as well as another inner cylinder at the rear of the front seal 126. Additional variations are also discussed below in relation to FIGS. 2-6.

Figure 2:
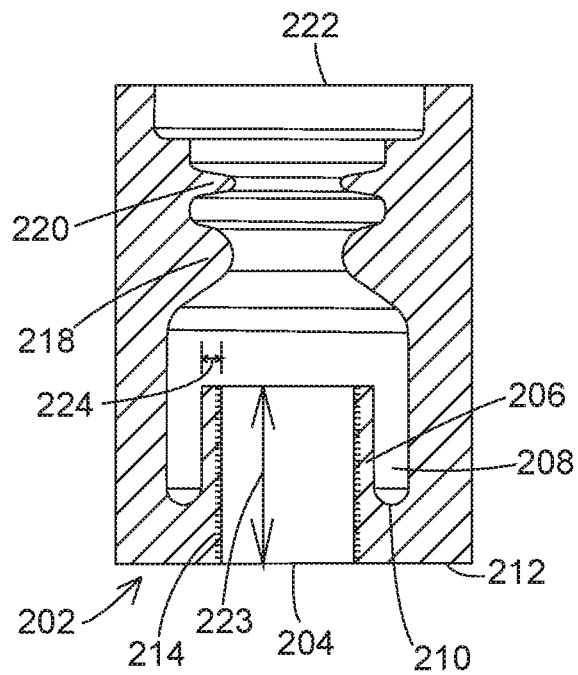
FIG. 2 shows a cross-sectional top view of a first example of a seal that includes a long contact length inner cylinder that is coupled to a front wall.

FIG. 2 shows an example of a seal 202, which may be the front seal 126 of FIG. 1 or may be a seal in a different location within the header 112, that includes an inner cylinder 206 having a transition portion 210 at a front wall 212. The seal 202 defines the bore opening 204 and has a gap 208 between inner cylinder 206 and the outer cylinder formed by the seal body. The inner cylinder 206 of this example lacks any inner protrusions which results in a more complete contact over the length of the inner cylinder 206 to the lead body. To facilitate the ingress and egress of the lead body through the cylinder 206 for some embodiments of the seal 202, the inner surface of the cylinder 206 may include a surface coating 214 to provide a lower friction. Examples of this surface coating include siloxane and parylene. As discussed above in relation to FIG. 1, rather than or in addition to the surface coating 214, the lead body 108 may include the surface coating 109 to reduce friction. This example also includes additional seals 218, 220 and defines a rear opening 222.

The cylinder 206 of the seal 202 is constructed to be a "long contact seal" that has reduced average contact pressure while having a contact length longer than conventional seals. Conventional seals typically have a contact length of about 0.005 inches, where contact length is the length of the portion of the seal, substantially along its longitudinal axis, that comes in contact with the structure received by the seal. In contrast, an example seal according to an embodiment of the current disclosure may have a contact length (shown as contact length 223 in FIG. 2) of at least 0.010 inches, at least 0.025 inches, or at least 0.050 inches.

A long contact seal may be constructed to have an average contact pressure that is within ranges acceptable to accommodate reasonable insertion forces when a structure is inserted into the seal (e.g., when a lead body is inserted into seal 202). In one example, such a seal may be configured to have an average contact pressure of no greater than K/contact length where "K" is 10 pounds per inch. In accordance with this, a seal having a contact length of at least 0.010 inches will exhibit an average contract pressure of no greater than 1000 pounds per square inch, while a seal having a contact length of at least 0.025 inches will exhibit an average contact pressure of no greater than 400 psi, and so on. Contact pressure is the pressure exerted by the seal in a substantially perpendicular direction against a structure located within, and making contact with, the inner portion of the seal (e.g., making contact with cylinder 206 of seal 202). Such a structure within cylinder may comprise a body and/or connector of a therapy delivery element such as a lead, lead extension, catheter, or other element for delivering therapy to the patient. Average contact pressure is the integral of the contact pressure over the area of contact between the seal and the structure located within the seal divided by that area of contact.

A seal according to one embodiment of this disclosure may be formed of a material with a tensile modulus of elasticity at 5% engineering strain that is between 100 and 1000 pounds per square inch (psi), or between 400 and 2500 psi, or between 1500 and 2100 psi, to reduce the contact pressure occurring between the inner cylinder 206 and a structure positioned within, and making contact with, inner cylinder. In one example, cylinder 206 may be formed of a silicone rubber having a durometer of 20A-90A. Alternatively, cylinder 206 may be formed of a polyurethane such as 80A polyurethane. Cylinder 206 may have a wall thickness 224 when cylinder is not under strain of 0.008 inches to 0.030 inches. The header may also be formed of a same material as cylinder 206.

A seal having a length of at least 0.010 inches, at least 0.025 inches or at least 0.050 inches and exhibiting an average contact pressure of no greater than (10 pounds per inch)/(contact length) may have an insertion force requirement ranging from 0.05 to 0.5 pounds per seal or between 0.03 to 0.3 pounds per seal.

Figure 2A:
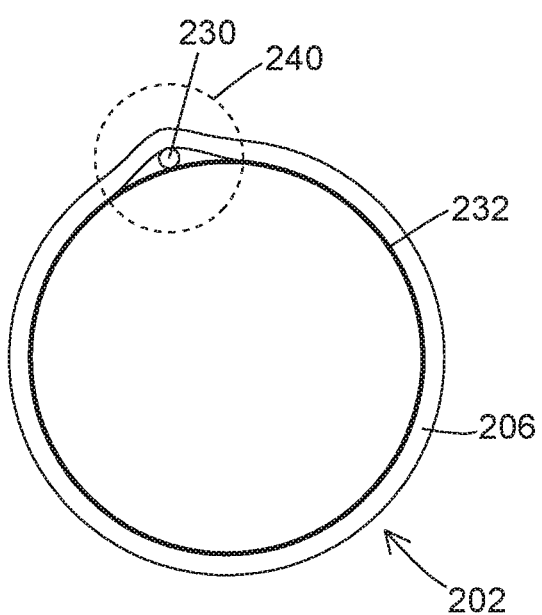
FIGS. 2A and 2B are enlarged cross-sectional views of a seal of FIG. 2 that is trapping a debris filament between the inner cylinder and a structure inserted within the inner cylinder.

A long contact seal having a contact length of 0.010 inches or more with an average contact pressure determined as K divided by contact length where K is ten pounds per inch, provides adequate electrical isolation, even when debris such as elongate polymer molding filaments are present between the seal 202 and a structure like a lead body inserted within the cylinder of the seal. FIG. 2A is an enlarged cross-sectional view of the cylinder 206 of seal 202 taken at a midpoint as shown in FIG. 2. A debris filament 230 is shown trapped between cylinder 206 and a structure 232 (e.g., lead body or extension body) inserted within, and contacting the inner surface of the cylinder 206. In some cases, this filament may extend along the length 223 (FIG. 2) of the seal 202 to form a fluid leakage pathway.

Figure 2B:
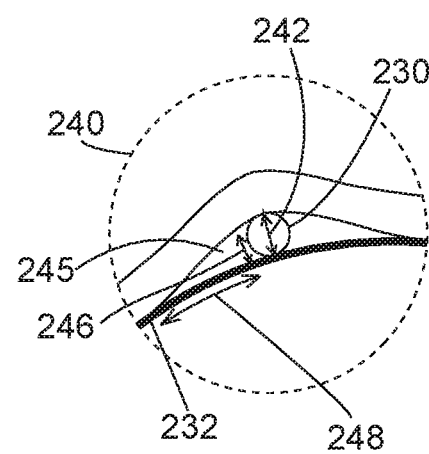

FIG. 2B is a magnified view of portion 240 (shown dashed) of FIG. 2A. For an example debris filament that has a diameter 242 of 0.001" and that is trapped between cylinder 206 of seal 202 and a structure 232 (e.g., lead body) within cylinder 206 of that seal, a gap 245 that may be substantially triangular in shape having a height 246 which may be about 0.001 inches and may have a width 248 of about 0.002 inches is created on each side of the filament. The cross-sectional area for each such gap is about 1×10E-06 square inches. Assuming that the debris filament extends the length 223 of the cylinder 206 of the seal 202 and if the electrical resistivity of body fluid is about 30 Ω-inches, then the resistivity of the fluid pathway formed along the seal length by each gap is (30 Ω-inches)×(seal contact length)/(0.000001 inches$^2$). For a typical lip seal with a contact length of 0.005 inches, resistivity of the fluid pathway would be about 150 kΩ. However, for a contact length of 0.010 inches or greater, a resistivity of at least 300 kΩ may be achieved. For contact lengths of 0.025 inches or greater or 0.050 inches or greater, a resistivity of at least 750 kΩ and at least 1.5 megΩ, respectively, may be achieved for each leakage pathway. For this example wherein an electrical leakage pathway exists on each side of the debris filament, total resistivity is 75 kΩ for the typical lip seal, but is at least 150 kΩ for a long contact seal having a length of at least 0.010 inches, and is at least 375 kΩ and at least 750 kΩ, respectively, for the contact seal having a length of at least 0.025 inches and at least 0.050 inches, respectively. Thus, the long contact seal may provide adequate electrical isolation even in an environment that allows for fluid ingress.

The wall portion 212 defines the transition portion 210 between the end of the inner cylinder 206 and the end of the outer cylinder that surrounds the inner cylinder 206 in this example. Because the rear end of the inner cylinder 206 is unattached, the transition portion 210 may serve as a hinge-like connection of the inner cylinder 206 to the wall portion 212. As the seal 202 is an elastic body, the transition portion 210 allows the rear end of the inner cylinder 206 to have freedom of movement within the gap 208 which allows the inner cylinder 206 to remain in sealing engagement with the lead body 108 as the lead body 108 may move about. The transition portions of the additional examples discussed below in FIGS. 3-6 may also offer this hinge-like connection that provides the inner cylinder of those examples with freedom of movement to remain in sealing engagement with the lead body 108.

Figure 3:
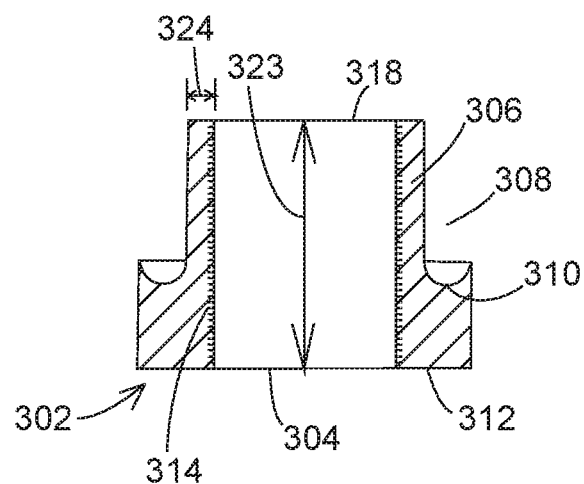
FIG. 3 shows a cross-sectional top view of a second example of a seal that includes a long contact length inner cylinder where no additional seals are present beyond the inner cylinder and where the inner cylinder is coupled to a front wall.

A long-contact seal such as described in reference to FIG. 2 may also be incorporated into other seal configurations described herein including those shown in FIGS. 3-6. FIG. 3 shows an example of a seal 302 that includes an inner cylinder 306 having a transition portion 310 at a front wall 312. The seal 302 defines the bore opening 304 and has a gap 308 between the inner cylinder 306 and the header structure surrounding the seal body. The inner cylinder 306 of this example lacks an inner protrusion which results in a more complete contact over the length of the inner cylinder 306 to the lead body. To facilitate the ingress and egress of the lead body through the cylinder 306 in some embodiments of the seal 302, the inner surface of the cylinder 306 may include a surface coating 314 like the surface coating 214 of FIG. 2 to provide a lower friction. As discussed above in relation to FIGS. 1 and 2, rather than or in addition to the surface coating 314, the lead body 108 may include the surface coating 109 to reduce friction. This example lacks any additional seals and the inner cylinder 306 defines a rear opening 318 of the seal.

Cylinder 306 of seal 302 having a contact length 323 and width 324 when a structure is inserted within cylinder 306 may also be constructed as a long contact seal. Cylinder 306 may have a contact length of at least 0.010 inches, of at least 0.025 inches, or at least 0.050 inches and have an average contact pressure of (10 pounds per inch)/contact length. Cylinder may be made of a material having a tensile modulus of elasticity at an engineering strain of 5% of 100 to 1000 psi, of 400 to 2500 psi, or of 1500 to 2100 psi. This long-contact seal may be combined with one or more of the other features described herein, allowing seal 302 to provide improved electrical isolation while also improving ability for a structure inserted within cylinder 306 (e.g., a lead or lead extension) to move laterally.

Seals disclosed herein, including long contact seals having an average contact pressure of 200 psi or less may be used in various locations within the header. Such seals may be used as the front seal that provides electrical isolation from the electrical connector and the body tissues and fluids immediately surrounding the device. Such seals may also be used between electrical connectors within the lead bore of the header to provide electrical isolation between the connectors without overly increasing insertion force of the lead. While the lateral motion of the lead body that reduces the effectiveness of a conventional front seal may be a lesser concern deeper into the lead bore of the header, debris between the lead body and the seal remains a concern. Therefore, this lengthy contact between the cylinder 306 of the seal 302 and the lead body provides a sealing benefit for these additional seal locations.

Figure 4:
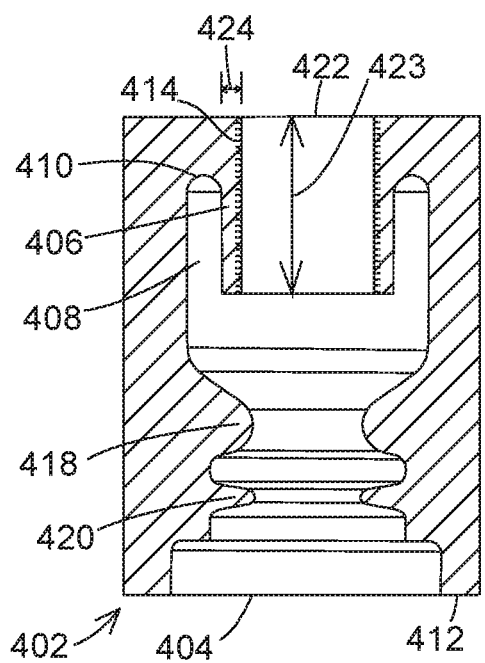
FIG. 4 shows a cross-sectional top view of a third example of a seal that includes a long contact length inner cylinder where the inner cylinder is coupled to a rear wall.

Likewise, FIG. 4 shows an example of a seal 402 that includes an inner cylinder 406 having a transition portion 410 at a rear wall. The front wall 412 of the seal 402 defines the bore opening 404. A gap 408 is formed between the inner cylinder 406 and the outer cylinder formed by the seal body. The inner cylinder 406 of this example lacks an inner protrusion which results in a more complete contact over the length of the inner cylinder 406 to the lead body. To facilitate the ingress and egress of the lead body through the cylinder 406 in this example, the inner surface of the cylinder 406 may include a surface coating 414 like the surface coating 214 of FIG. 2 to provide a lower friction. As discussed above in relation to FIGS. 1 and 2, rather than or in addition to the surface coating 414, the lead body 108 may include the surface coating 109 to reduce friction. This example also includes additional seals 418, 420, and the inner cylinder 406 defines a rear opening 422 of the seal. Cylinder 406 of seal 402 having a contact length 423 and width 424 when a structure is inserted within cylinder 406 may also be constructed as a long contact seal. Cylinder 406 may have a contact length of at least 0.010 inches, of at least 0.025 inches, or at least 0.050 inches and have an average contact pressure of (10 pounds per inch)/contact length. Cylinder may be made of a material having a tensile modulus of elasticity at an engineering strain of 5% of 100 to 1000 psi, of 400 to 2500 psi, or of 1500 to 2100 psi. This long-contact seal may be combined with one or more of the other features described herein, allowing seal 402 to provide improved electrical isolation while also improving ability for a structure inserted within cylinder 406 (e.g., a lead or lead extension) to move laterally.

Figure 5:
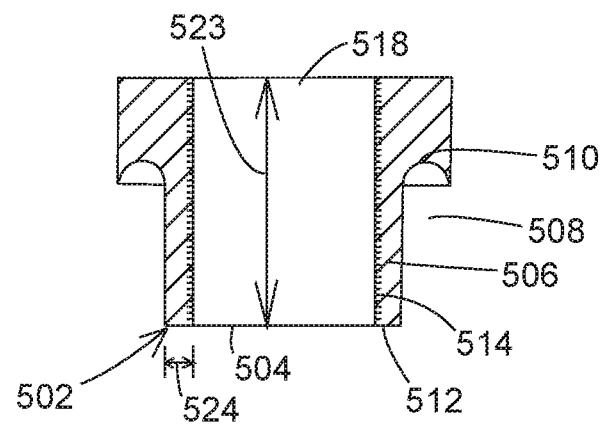
FIG. 5 shows a cross-sectional top view of a fourth example of a seal that includes a long contact length inner cylinder where no additional seals are present beyond the inner cylinder and where the inner cylinder is coupled to a rear wall.

FIG. 5 shows an example of a seal 502 that includes an inner cylinder 506 having a transition portion 510 at a rear wall. The front end 512 of the inner cylinder 506 defines the bore opening 504. The seal 502 has a gap 508 between the inner cylinder 506 and the header structure surrounding the seal body. The inner cylinder 506 of this example lacks an inner protrusion which results in a more complete contact over the length of the inner cylinder 506 to the lead body. To facilitate the ingress and egress of the lead body through the cylinder 506 in some embodiments of the seal 502, the inner surface of the cylinder 506 may include a surface coating 514 like the surface coating 214 of FIG. 2 to provide a lower friction. As discussed above in relation to FIGS. 1 and 2, rather than or in addition to the surface coating 514, the lead body 108 may include the surface coating 109 to reduce friction. This example lacks any additional seals and the rear wall of the seal 502 defines a rear opening 518 of the seal.

Cylinder 506 of seal 502 having a contact length 523 and width 524 when a structure is inserted within cylinder 406 may also be constructed as a long contact seal. Cylinder 506 may have a contact length of at least 0.010 inches, of at least 0.025 inches, or at least 0.050 inches and have an average contact pressure of (10 pounds per inch)/contact length. Cylinder may be made of a material having a tensile modulus of elasticity at an engineering strain of 5% of 100 to 1000 psi, of 400 to 2500 psi, or of 1500 to 2100 psi. This long-contact seal may be combined with one or more of the other features described herein, allowing seal 502 to provide improved electrical isolation while also improving ability for a structure inserted within cylinder 506 (e.g., a lead or lead extension) to move laterally.

Figure 6:
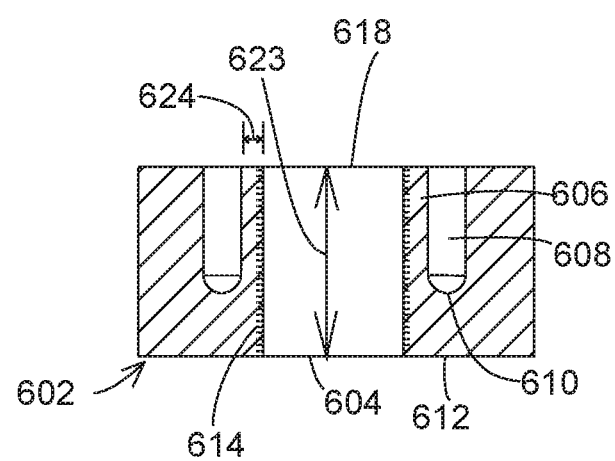
FIG. 6 shows a cross-sectional top view of a fifth example of a seal that includes a long contact length inner cylinder where no additional seals are present beyond the inner cylinder but where a full-length outer cylinder is present and where the inner cylinder is coupled to a front wall.

FIG. 6 shows an example of a seal 602 that includes an inner cylinder 606 that extends the full-length of the seal 602 and where the outer cylinder surrounds the inner cylinder 606 over the full length of the seal 602. The inner cylinder 606 has a transition portion 610 at a front wall 612. The seal 602 defines the bore opening 604 and has a gap 608 between the inner cylinder 606 and the outer cylinder surrounding the seal body. The inner cylinder 606 of this example lacks an inner protrusion which results in a more complete contact over the length of the inner cylinder 606 to the lead body. To facilitate the ingress and egress of the lead body through the cylinder 606, the inner surface of the cylinder 606 may include a surface coating 614 like the surface coating 214 of FIG. 2 to provide a lower friction. As discussed above in relation to FIGS. 1 and 2, rather than or in addition to the surface coating 614, the lead body 108 may include the surface coating 109 to reduce friction. This example lacks any additional seals and the inner cylinder 606 defines a rear opening 618 of the seal although it is present within the full-length outer cylinder.

Like the seals 202, 302, 402, and 502 discussed above, the seal 602 of FIG. 6 may be sized as a long contact seal having an average contact pressure of no greater than (10 pounds per inch)/contact length. Such a seal may have a contact length of at least 0.010 inches, at least 0.025 inches, or at least 0.05 inches. Such a seal creates a reduced contact pressure on the lead body as an alternative to or in addition to the surface coating 614. This seal 602 may also be useful for maintaining adequate electrical isolation, even when debris filaments are present, at various locations including the front seal position as well as positions between electrical connectors deeper into the lead bore of the header. Such a seal may be formed of a material having a tensile modulus of elasticity at engineering strain of 5% of 100 to 1000 psi, of 400 to 2500 psi, or of 1500 to 2100 psi. In some examples, such a seal is formed of silicone rubber having a hardness of 20A-90A or a polyurethane such a polyurethane 80A.

It will be understood that the examples of FIGS. 2-6 are providing examples of seal configurations that utilize long contact seals. It will be understood that long contact seals may be incorporated into many other seal configurations not shown herein, including at any seal location wherein the contact length substantially along the longitudinal axis of the seal (e.g., the axis of the seal that would generally be parallel to a longitudinal axis of a structure inserted into the seal) can be increased to 0.010 inches or greater. A determination as to whether the increase in length may be accommodated may be based, in some cases, on spacing of electrical contacts on a structure to be received by the seal.

The embodiments described above in FIGS. 1-6 also apply to lead extensions in addition to device headers. For instance, lead extensions may include a distal end that forms a housing that provides a lead bore containing electrical connectors much like a device header. The proximal end of the lead may be inserted into the lead bore of the extension in the same manner as inserting the lead into the lead bore of a device header. Therefore, any discussion of utilizing a seal within a lead bore of a device header as discussed herein should be considered to also apply to utilizing a seal within a lead bore of a lead extension. Furthermore, the proximal end of a lead extension is inserted into the lead bore of the device header and therefore the seal of the device header may operate in conjunction with the lead body of the lead extension to form a seal in the same manner as if a lead had been inserted into the lead bore of the device header.

While embodiments have been particularly shown and described, it will be understood by those skilled in the art that various other changes in the form and details may be made therein without departing from the spirit and scope of the invention.

What is claimed is:

1. An implantable medical system, comprising:
   a therapy delivery element having a proximal contact, a body, and a length;
   a housing defining a first bore, the therapy delivery element being present within the first bore;
   circuitry within the housing to at least one of deliver therapy to a patient or sense a biological signal of the patient;
   an electrical connector positioned within the first bore and electrically coupled to the circuitry, with the proximal contact being in contact with the electrical connector; and
   a monolithic elastic seal body coupled to the housing and having a wall that provides an outer surface of a portion of the housing, the monolithic elastic seal body comprising a first cylinder defining a seal bore, the first cylinder being positioned within the first bore and contacting the length of the therapy delivery element over a contact length of at least 0.010 inches and with an average contact pressure of no greater than (10 pounds per inch)/(contact length).

2. The implantable medical system of 1, wherein the contact length is at least 0.025 inches.

3. The implantable medical system of 1, wherein the contact length is at least 0.050 inches.

4. The implantable medical system of claim 1, wherein the first cylinder is formed of a material having a tensile modulus of elasticity of 100 to 1000 pounds per square inch at an engineering strain of 5%.

5. The implantable medical system of claim 1, wherein the elastic seal body is formed of silicone rubber having a hardness of 20A to 90A.

6. The implantable medical system of claim 1, wherein the first cylinder has a cylinder wall having a thickness of 0.008 inches to 0.030 inches.

7. The implantable medical system of claim 1, wherein at least a portion of the elastic seal body is formed to define a gap between at least a portion of the first cylinder and the first bore.

8. A method of providing electrical isolation of an electrical contact of a therapy delivery element within a surrounding structure having a first bore containing an electrical connector with the therapy delivery element being present within the first bore, circuitry being present within the housing to at least one of deliver therapy to a patient or sense a biological signal of the patient, and with the electrical connector being positioned within the first bore and electrically coupled to the circuitry, with the proximal contact being in contact with the electrical connector, the method comprising:
   providing a monolithic elastic seal body within the first bore and coupled to the surrounding structure, the monolithic elastic seal body comprising a first cylinder defining a seal bore configured to receive a portion of the therapy delivery element and to establish electrical contact between the therapy delivery element and the electrical connector of the first bore, and further providing an outer surface of a portion of the housing with a wall of the elastic seal body; and
   creating contact of the first cylinder with the portion of the therapy delivery element over a contact length of at least 0.010 inches with an average contact pressure of no greater than (10 pounds per inch)/(contact length) when the portion of the therapy delivery element is received by the first cylinder.

9. The method of claim 8, wherein the surrounding structure is a distal end of a lead extension.

10. The method of claim 8 wherein the surrounding structure is a device header of a medical device.

11. The method of claim 8, wherein the contact length is at least 0.025 inches.

12. The method of claim 8, wherein the contact length is at least 0.050 inches.

13. The method of claim 8, wherein the first cylinder is formed of a material having a tensile modulus of elasticity of 100 to 1000 pounds per square inch at an engineering strain of 5%.

14. The method of claim 8, wherein the elastic seal body is formed of silicone rubber having a hardness of 20A to 90A.

15. The method of claim 8, wherein at least a portion of the elastic seal body is formed to define a gap between at least a portion of the first cylinder and the first bore.

16. An implantable medical system, comprising:
   a lead having a proximal contact and a lead body;
   a lead extension comprising a distal end structure defining a lead bore containing an electrical connector and at least one monolithic elastic seal body, the at least one monolithic elastic seal body having a wall that provides an outer surface of a portion of the lead extension, the monolithic elastic seal body comprising a first cylinder, wherein the lead is present within the lead bore such that the proximal contact makes contact with the electrical connector and wherein the first cylinder contacts the lead body over a contact length of at least 0.010 inches and with an average contact pressure of no greater than (10 pounds per inch)/(contact length).

17. The implantable medical system of 16, wherein the contact length is at least 0.025 inches.

18. The implantable medical system of 16, wherein the contact length is at least 0.050 inches.

19. The implantable medical system of claim 16, wherein the first cylinder is formed of a material having a tensile modulus of elasticity of 100 to 1000 pounds per square inch at an engineering strain of 5%.

20. The implantable medical system of claim 16, wherein the first cylinder is formed of a material having a tensile modulus of elasticity of 400 to 2500 pounds per square inch at an engineering strain of 5%.

* * * * *